United States Patent
Mitra et al.

(10) Patent No.: US 7,435,430 B2
(45) Date of Patent: Oct. 14, 2008

(54) NATURAL SEDATIVE COMPOSITION, PROCESS FOR OBTAINING THE SAME AND PHARMACEUTICAL FORMULATIONS THEREOF

(75) Inventors: Shankar Kumar Mitra, Karnataka (IN); Ekta Saxena, Karnataka (IN); Marikunte Venkata Ranganna, Karnataka (IN)

(73) Assignee: MMI Corporation, Grand Cayman Islands, British West Indies ( * ) Notice: Subject to any disclaimer, the term of this patent is extended or adjusted under 35 U.S.C. 154(b) by 92 days.

(21) Appl. No.: 10/900,203

(22) Filed: Jul. 28, 2004

(65) Prior Publication Data
US 2005/0266101 A1 Dec. 1, 2005

(30) Foreign Application Priority Data
May 28, 2004 (IN) .................. 973/DEL/2004

(51) Int. Cl.
*A61K 36/00* (2006.01)
(52) U.S. Cl. .................. 424/725; 424/776; 424/777
(58) Field of Classification Search .................. None
See application file for complete search history.

(56) References Cited

U.S. PATENT DOCUMENTS

| | | | |
|---|---|---|---|
| 4,671,959 A | * | 6/1987 | Warren et al. ............. 424/769 |
| 4,752,476 A | * | 6/1988 | Copney .................. 424/745 |
| 2003/0180395 A1 | * | 9/2003 | Bueter .................. 424/725 |

OTHER PUBLICATIONS

Hoodia Advice: Hoodia Gordonii—The Big Picture, accessed Oct. 12, 2006 from URL<http://www.hoodia-advice.org/hoodia-gordonii.html> pp. 1-3.*
MacPhillamy, H. B.: Drugs from Plants: Plant Science Bulletin, Apr. 1963, vol. 9, Issue 2 pp. 1-15 from internet: URL<http://www.botany.org/PlantScienceBulletin/psb-1963-9-2.php>.*
Phillipson, J. New Drugs From Nature—It Could Be Yew; Phytotherapy Research 13 (1999) pp. 2-8.*
Raskin et al. Can an apple a Day Keep the Doctor Away?: Current Pharmaceutical Design (2004), 10, pp. 3419-3429.*
Revilla et al. Comparison of Several Procedures Used for the Extraction of Anthocynains From Red Grapes; J. Agric. Food Chem. 1998, 46, pp. 4592-4597.*

* cited by examiner

*Primary Examiner*—Patricia Leith
(74) *Attorney, Agent, or Firm*—Darby & Darby PC

(57) ABSTRACT

Disclosed is a natural sedative composition for the treatment of insomnia, anxiety, stress and all kinds of sleep disorders, the composition comprising extract of plant *Myristica fragrans* and/or plant *Hedychium spicatum* and a pharmaceutically acceptable carrier. Also disclosed are methods for obtaining the plant extract and dosage forms.

14 Claims, 3 Drawing Sheets

NATURAL SEDATIVE COMPOSITION, PROCESS FOR OBTAINING THE SAME AND PHARMACEUTICAL FORMULATIONS THEREOF

FIELD OF THE INVENTION

In general, this invention relates to pharmaceutical formulations comprising sedatives. More particularly, the present invention discloses a natural sedative composition comprising, solvent extract of seeds of *Myristica fragrans* and/or rhizomes of *Hedychium spicatum* and a pharmaceutically acceptable carrier, methods of obtaining the same and use thereof for treating sleep disorder, stress, anxiety, depression and schizophrenia.

BACKGROUND OF THE INVENTION

Insomnia, a sleep disorder is a serious problem for millions of adults worldwide. Sleep and sleep-related problems play a major role in a large number of human disorders and affect almost every field of medicine.

Sleeping problems are common in many other disorders as well, including Alzheimer's disease, stroke, cancer, and head injury. These sleeping problems may arise from changes in the brain regions and neurotransmitters that control sleep, or from the drugs used to control symptoms of other disorders. In patients who are hospitalized or who receive round-the-clock care, treatment schedules or hospital routines also may disrupt sleep.

Synthetic sleeping agents like barbiturates and carbamates are associated with side effects like dependence, severe acute intoxication on overdoses. Today the benzodiazepines series of drugs like diazepam and chlordiazepoxide are the major drugs used for the treatment of anxiety and insomnia.

To overcome the major side effects of synthetic anti anxiety and sedative drugs, research has been directed towards the development of safe and effective natural compositions for insomnia, anxiety and stress etc. This invention is aimed to develop natural and safe composition for treating various sleep disorders in humans.

RELATED ART

The Chloroform extract of Nutmeg (*Myristica fragrans*) has been evaluated for antiinflammatory, analgesic and antithrombic activities in rodents (Phytotherapy Res. 13(4), 344-45, 1999). Olajide O A et al., reported the effects of nutmeg in albino rabbits for hyperlipidaemia. *Myristica fragrans* extract also reported to show platelet anti aggregatory activity. (Ram, A. et al., J. of Ethnopharmacology, 55(1), 49-53, 1996; Janssens, J. et al., J. of Ethnopharmacol, 29(2), 179-88, 1990).

The 50% ethanol extract of *M. fragrans* (nutmeg) was studied by Tajuddin et al., in male mice for aphrodisiac activity (BMC complement Altern Med. 3(1), 6, 2003).

Sherry, C. J. et al., reported the enhancement of ethanol-induced sleep by whole oil of nutmeg in young chickens and a ligroin extract of nutmeg caused a significant increase in the duration of light and deep sleep in the young chicken. (Experientia, 37(4), 492-3, 1978; J. Ethnopharmacology, 6(1), 61-66, 1982).

Messiha, F. S. et al., reported the CNS depressant action of nutmeg by behavioural performance test, whereas Truitt, et al., reported evidences of monooxidase inhibition by nutmeg (Vet Hum Toxicol, 26(2), 17-20, 1984; Proc. Soc. Exp. Bio. Med. 112, 647-50, 1963).

In 1994, Van Gil, S. C. et al., reported that there was no experimental evidence to support previous findings of nutmeg having hallucinogenic or other psychotropic properties, but instead it showed a mild sedative effect (J. Ethnopharmacology, 42(2), 117-24, 1994).

Recently, Grover, J. K. et al., reported that nutmeg crude suspension (NMC) and petroleum ether extract (PE) had a good antidiarrhoeal effect and sedative property (Methods Find Exp Clin Pharmacol, 24(10), 675-80, 2002).

Sonavane, et al., reported that Hexane and Acetone insoluble extracts of nutmeg show non specific anxiogenic activity (Pharmacol Biochem Behav, 71 (1-2), 239-44, 2002).

U.S. Pat. No. 4,752,476 to Copney, et al., describes a composition, which comprises of two teaspoons of nutmeg, rose water, bay leaves and spearmint, to be ingested after boiling, by an individual for inducing sleep.

U.S. Pat. No. 4,671,959 to Warren, et al., teaches a method of reducing physiological and/or subjective reactivity to stress in human beings subjected to stress conditions. The method comprises administering of a composition of Nutmeg Oil, Mace Extract, Neroli Oil, Valerian Oil, Myristicin, Isoelemicin and Elemicin either through inhalation or transdermally, using one or more of the above ingredients alone or in a suitable composition such as ethanol and/or a perfume composition, cologne or perfumed article (e.g., air freshener or deodorant stick).

SUMMARY OF THE INVENTION

It is the principal aspect of the present invention to disclose the sedative effects of the extracts of plant *Myristica fragrans* and plant *Hedychium spicatum*.

In another aspect, the present invention discloses the efficacy of the extracts of plant *Myristica fragrans* and plant *Hedychium spicatum* as anti stress and sleep inducing agents.

In still another aspect, the present invention provides for a pharmaceutical composition containing a therapeutically effective amount of extracts of *Myristica fragrans* and *Hedychium spicatum*.

In yet another aspect, the present invention provides for a pharmaceutical composition containing a therapeutically effective amount of extracts of plants *Myristica fragrans* and *Hedychium spicatum* or a pharmaceutical composition comprising said extract of said plants, in a pharmaceutically acceptable carrier or otherwise.

In one another aspect, the present invention provides for determining the role of a therapeutically effective amount of extracts of plants *Myristica fragrans* and *Hedychium spicatum* in anxiety and sleep disorders.

In one another aspect, the present invention discloses methods of producing extracts from plant *Myristica fragrans* and plant *Hedychium spicatum*.

In one preferred embodiment, there is provided a natural sedative composition comprising a therapeutically effective amount of the extract of plant *Myristica fragrans* and plant *Hedychium spicatum*, wherein the extract is prepared by all parts of said herb *Myristica fragrans* and preferably its seeds.

In another preferred embodiment, there is provided a natural sedative composition comprising a therapeutically effective amount of the extract of plants *Myristica fragrans* and *Hedychium spicatum*, wherein the extract is prepared by all parts of said herb *Hedychium spicatum* and preferably its rhizomes.

In one another preferred embodiment, there is provided a natural sedative composition comprising an organic solvent extract, using all kinds of solvents from n-hexane to polar solvents methanol and ethyl alcohol and preferably methanol, of the coarse powder of seeds of plant *Myristica fragrans*.

In one another preferred embodiment, there is provided a natural sedative composition comprising an organic solvent extract, using all kinds of solvents from n-hexane to polar solvents methanol and preferably n-hexane, of the coarse powder of rhizomes of plant *Hedychium spicatum*.

In yet another preferred embodiment, there is provided a natural sedative composition comprising a therapeutically effective amount of methanol extract of *Myristica fragrans* and n-hexane extract of *Hedychium spicatum* and other pharmaceutically acceptable carriers.

In another preferred embodiment, there is provided a natural sedative composition comprising a therapeutically effective amount of methanol extract of *Myristica fragrans*, n-hexane extract of *Hedychium spicatum*, ajowan oil and Lavender oil and other pharmaceutically acceptable carriers.

In yet another preferred embodiment, there is provided a natural sedative composition comprising a therapeutically effective amount of methanol extract of *Myristica fragrans*, ajowan oil, Lavender oil and other pharmaceutically acceptable carriers.

In yet another preferred embodiment, there is provided a natural sedative composition comprising a therapeutically effective amount of hexane extract of *Hedychium spicatum*, ajowan oil, Lavender oil and other pharmaceutically acceptable carriers.

In yet another preferred embodiment, there is provided a natural sedative composition comprising a therapeutically effective amount of methanol extract of *Myristica fragrans* (3 parts), hexane extract of *Hedychium spicatum* (1 part), ajowan oil (2.5%), Lavender oil (5%) and other pharmaceutically acceptable carriers.

In another preferred embodiment, there is provided a method of obtaining the active fraction of extracts of *Myristica fragrans* by subjecting the extract to careful separation of thick oil from the resinous matter settled down.

In another preferred embodiment, there is provided a method of obtaining the active fraction of extracts of *Hedychium spicatum* by subjecting the extract to repeated crystallization and removal of active thin oil portion from crystalline matter by muslin cloth filtration.

In yet another preferred embodiment, there is provided a natural sedative composition containing a therapeutically effective amount of extracts of plants *Myristica fragrans, Hedychium spicatum*, ajowan oil and lavender oil in a pharmaceutically acceptable carrier wherein the composition is in an oral dosage form preferably softgel capsules.

In another preferred embodiment, there is provided a natural sedative composition containing a therapeutically effective amount of extracts of plants *Myristica fragrans, Hedychium spicatum*, ajowan oil and lavender oil in an amount of 50 mg to 500 mg and pharmaceutically acceptable carriers comprising Butylated Hydroxy Toluene IP (0.02%), Methyl paraben sodium (0.01 mg), Propyl paraben sodium (0.0025 mg), per soft gel capsule, preferably Die size & shape 5J oval and gel color, Light Brown Opaque.

In another preferred embodiment, there is provided a delivery system containing natural sedative composition, wherein the delivery system comprises tablets, softgel capsules, granules and syrups, powders, concentrates, dry syrups etc.

In yet another preferred embodiment, there is provided a natural sedative composition comprising a potency equivalent of the extract ranging from about 5 mg to about 500 mg.

In a still preferred embodiment, there is provided a method of treating anxiety, stress, convulsions, sleep disorders and interrupted sleep by administering to a patient a natural sedative composition comprising a therapeutically effective amount of extracts of plants *Myristica fragrans* and *Hedychium spicatum*, ajowan oil, lavender oil in a pharmaceutically acceptable carrier or otherwise.

In still another preferred embodiment, there is provided a process for obtaining a natural sedative composition, the process comprising extracting Myristica fragrans seeds by percolation, filtering the plant extract, concentrating the plant extract to dryness on rotatory evaporator or on steam bath at optimum temperature and careful separation of thick oil portion from inactive resinous matter producing a herbal composition comprising the said extract and pharmaceutically acceptable carrier.

In still another preferred embodiment, there is provided a process for obtaining a natural sedative composition, the process comprising extracting Myristica fragrans seeds by hot soxhalation, filtering the plant extract, concentrating the plant extract to dryness on rotatory evaporator or on steam bath at optimum temperature and careful separation of thick oil portion from inactive resinous matter producing a herbal composition comprising the said extract and pharmaceutically acceptable carrier.

In still another preferred embodiment of the present invention, there is provided a process for preparation of a novel herbal composition. The method comprising, extracting plant extract from the rhizomes of *Hedychium spicatum* by percolation, filtering the plant extract, concentrating the plant extract to dryness on rotatory evaporator or on steam bath at optimum temperature and producing an oily extract free from any crystalline material, employing the said extract and pharmaceutically acceptable carrier.

In still another preferred embodiment of the present invention, there is provided a process for preparation of a novel herbal composition. The method comprising extracting plant extract from the rhizomes of *Hedychium spicatum* by hot soxhalation, filtering the plant extract, concentrating the plant extract to dryness on rotatory evaporator or on steam bath at optimum temperature and producing an oily extract free from any crystalline material, employing the said extract and pharmaceutically acceptable carrier.

DETAILED DESCRIPTION OF THE INVENTION

Figure 1:
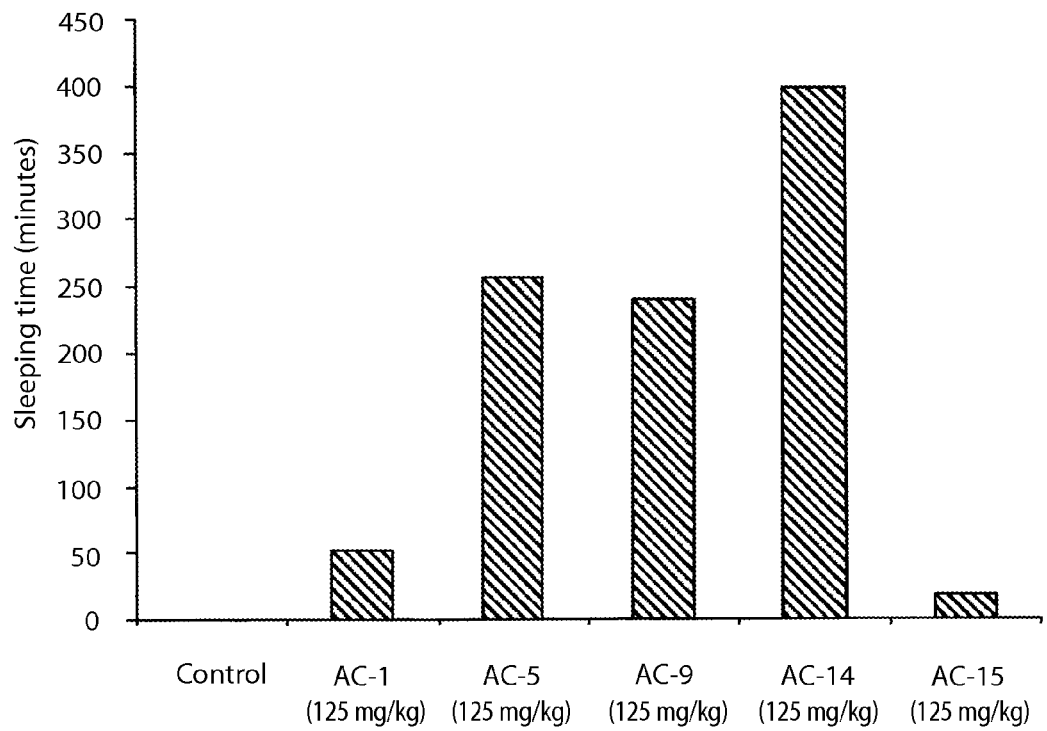
FIG. 1. Bar graph representation sowing effect of different solvent extracts on Pentobarbitone induced sleeping time.

The present invention involves the selection and identification of the herbs and obtaining the extract by subjecting the same to solvent extraction. The bioassay guided fractionation of the extract to identify the active markers or active fraction and to develop effective and safe composition for use in human beings in stress, anxiety and sleep disorders as a sedative.

*Myristica fragrans* Houtt, is a genus of trees distributed from India and South East Asia to North Australia and Pacific Islands. It is occasionally cultivated for its aril (mace) and seed (nutmeg) used as spice. Nutmeg and mace are used as condiment and in medicine. Nutmeg is stimulant, carminative, astringent and aphrodisiac. It is used in tonics and electuaries and forms a constituent of preparations prescribed for dysentery, stomach ache, flatulence, nausea, vomiting, malaria, rheumatism and early stages of leprosy (Burkill, 11, 1528-30; Kirt & Basu, III, 2141; B.P.C. 1959, 502; Nayar, J. Bombay Nat. Hist. Soc., 52, 515, 1954-55).

*Hedychium spicatum* rhizomes are stomachic, carminative, stimulant and tonic. They are used in dyspepsia. (Nadkarni, I, 608; Dastur, Useful plants, 122; Taylor & Dutt; Proc. Nat. Acad. Sci. India, 1940, 10A, 17). The dried rhizomes of commerce on steam distillation yield 4% of an essential oil and its main constituent being ethyl-p-methoxy cinnamate. The oil may be used as perfume for soaps; hair oils and face powders etc. (Taylor & Dutt, Loc. Cit; Dymock, Warden & Hooper, III, 419. Finnemore, 182; Wehner, I, 179, Chem Abstr; 1940, 3A, 6015). The presence of alkaloids, saponins and flavonoids has been reported in the rhizomes (Suchitra Kumar et al., J. Econ. Bot Phytochem, 1990, I, 13). The ethanolic extract of dried rhizomes showed antibacterial activity. (Venkata Narayana et al., Indian Med. 1989, 1, 6; Mishra et al., Int J Pharmacogn, 1991, 29, 19).

EXAMPLE 1

Preparation of extract from *Myristica Fragrans* By Percolation Method:

The dried material of seeds of *Myristica fragrans* was pulverized to coarse powder and about 5 Kg each of powdered material was placed in different flasks and extracted with petroleum ether, n-hexane, dichloromethane, chloroform, ethyl alcohol, ethyl acetate, acetone, water and methanol at room temperature for 24 h to 48 h, then plant extracts were filtered and concentrated to dryness on rotatory evaporator or on steam bath at optimum temperature and under reduced pressure.

EXAMPLE 2

Preparation Of Extract From *Myristica Fragrans* By Hot Soxhalation Method:

The coarse powdered material of seeds of *Myristica fragrans* was subjected to hot soxhalation using solvents petroleum ether, n-hexane, dichloromethane, chloroform, ethyl alcohol, ethyl acetate, acetone and methanol, at optimum temperature and recycled until extraction was completed, then plant extracts were filtered and concentrated to dryness on rotatory evaporator or on steam bath at optimum temperature.

All extracts such as petroleum ether extract (AC-1) n-hexane extract (AC-2), dichloromethane extract (AC-3), chloroform extract (AC-4), ethyl alcohol extract (AC-5), ethyl acetate extract (AC-6), acetone extract (AC-7), water extract (AC-8) and methanol extract (AC-9) prepared from the seeds of *Myristica fragrans* by using percolation method or hot soxhalation method were subjected to HPTLC (High Performance Thin Layer Chromatography) and HPLC (High performance Liquid chromatography) and Gas Chromatography (GC) in various mobile phases on precoated TLC plates (Merck), ODS column and 10% Carbowax 20M (2 meter) GC column (Temp. 70-220° C.) respectively for qualitative and quantitative estimation of marker compounds and active principles. It was found that the extracts AC-1 to AC-9 were qualitatively and quantitatively similar to each other.

Different Solvent Extracts Of *Myristica Fragrans* Seeds

TABLE 1

| Sl. No. | Code | Name of the Extract | Nature of the Extract | Yield | Activity |
|---|---|---|---|---|---|
| 1. | AC-1 | Petroleum Ether Extract | White Solid | 14% | Slightly |
| 2. | AC-2 | Hexane Extract | White Solid | 16% | Inactive |

TABLE 1-continued

| Sl. No. | Code | Name of the Extract | Nature of the Extract | Yield | Activity |
|---|---|---|---|---|---|
| 3. | AC-3 | Dichloromethane Extract | Slight brown Oil | 22% | Inactive |
| 4. | AC-4 | Chloroform Extract | Yellow brown Oily Solid | 24% | Inactive |
| 5. | AC-5 | Ethyl Alcohol Extract | Upper Layer Brown Oily Liquid | 5% | Active |
| 6. | AC-6 | Ethyl Acetate Extract | Brown Oily Solid | 20% | Inactive |
| 7. | AC-7 | Acetone Extract | Brownish Oil | 5% | Inactive |
| 8. | AC-8 | Water Extract | Brown Viscous Mass | 2.5% | Inactive |
| 9. | AC-9 | Methanol Extract | Upper Brown Oily Liquid | 7.5% | Highly active |

EXAMPLE 3

GC-MS Studies Of AC-9 Extract

TABLE 2

| Sl. No. | RT (Min.) | M+ | Name | Molecular Formula | Composition (%) |
|---|---|---|---|---|---|
| 1. | 6.808 | 136 | Camphene or Limonene α & β pinene | $C_{10}H_{16}$ | 0.21 |
| 2. | 7.200 | 111 | 2-acetyl furan | $C_6H_6O_2$ | 0.47 |
| 3. | 7.922 | 154 | α-terpineol | $C_{10}H_{18}O$ | 1.54 |
| 4. | 8.075 | 162 | Safrole | $C_{10}H_{10}O_2$ | 0.21 |
| 5. | 8.783 | 136 | β-phellandrene | $C_{10}H_{16}$ | 1.40 |
| 6. | 9.183 | 164 | Eugenol | $C_{10}H_{12}O_2$ | 0.50 |
| 7. | 9.425 | 178 | Methyl eugenol | $C_{11}H_{14}O_2$ | 2.10 |
| 8. | 9.742 | 164 | Iso eugenol | $C_{10}H_{12}O_2$ | 1.09 |
| 9. | 9.933 | 178 | Butyl benzoate | $C_{11}H_{14}O_2$ | 0.44 |
| 10. | 10.142 | 192 | Myristin | $C_{11}H_{12}O_3$ | 14.43 |
| 11. | 10.233 | 208 | Elemicin | $C_{12}H_{16}O_3$ | 13.99 |
| 12. | 10.317 | 208 | Unknown | Unknown | 0.88 |
| 13. | 10.475 | 194 | Geranylacetone | $C_{13}H_{22}O$ | 1.76 |
| 14. | 10.692 | 208 | Unknown | Unknown | 1.36 |
| 15. | 11.142 | 199 | Citronellyl acetate | $C_{12}H_{22}O_2$ | 0.69 |
| 16. | 11.475 | 228 | Myristic acid | $C_{14}H_{28}O_2$ | 32.94 |
| 17. | 11.875 | 222 | α-caryophyllene alcohol | $C_{14}H_{22}O$ | 2.38 |
| 18. | 12.725 | 256 | Butyl dodecanoate | $C_{16}H_{32}O_2$ | 4.53 |
| 19. | 14.533 | 111 | Unknown | Unknown | 0.75 |

EXAMPLE 4

Preparation Of Extract From *Hedychium Spicatum* By Percolation Method

The dried material of rhizomes of *Hedychium spicatum* was pulverized to coarse powder and about 5 Kg each of powdered material was placed in different flasks and extracted with n-hexane, chloroform, ethyl acetate and methanol at room temperature for 24 h to 48 h, then plant extracts were filtered and concentrated to dryness on rotatory evaporator or on steam bath at optimum temperature and under reduced pressure.

EXAMPLE 5

Preparation Of Extract From *Hedychium Spicatum* By Hot Soxhalation Method:

The coarse powdered material of rhizomes of *Hedychium spicatum* was subjected to hot soxhalation using solvents n-hexane, chloroform, ethyl acetate and methanol at optimum temperature and recycled until extraction is completed, then plant extracts were filtered and concentrated to dryness on rotatory evaporator or on steam bath at optimum temperature.

All extracts such as n-hexane extract (AC-10), chloroform extract (AC-11), ethyl alcohol extract (AC-12) and methanol extract (AC-1 3) prepared from the rhizomes of *Hedychium spicatum* by using percolation method or hot soxhalation method were subjected to HPTLC (High Performance Thin Layer Chromatography) and HPLC (High performance Liquid chromatography) and Gas Chromatography (GC) in various mobile phases on precoated TLC plates (Merck), ODS column and 10% Carbowax 20M (2 meter) GC column (Temp. 70-220° C.) respectively for qualitative and quantitative estimation of marker compounds and active principles. It was found that the extracts AC-10 to AC-13 were qualitatively and quantitatively similar to each other.

EXAMPLE 6

Preliminary Screening Of Extracts For Sedative Activity

Animals

Albino swiss mice and rats of wistar strain bred in Experimental Animal Facility of R&D Center, The Himalaya Drug Company, were used for the experiment. The animals were maintained at 22±3° C., 50-60% of humidity, 12 hours light and dark cycle, with unlimited supply of drinking water and feed.

Potentiation Of Pentobarbitone Sleeping Time

Groups of 8 male mice with an average weight of 25-28 g are used. They are dosed orally, i.p. with the test compounds (AC-1 to 13) at a dose of 125 mg/kg by weight. Thirty minutes after i.p. injection, 40 mg/kg pentobarbital is injected intraperitonially. The animals are placed on their backs on a warmed (37° C.) pad and the duration of loss of the righting reflex (starting at the time of pentobarbital injection) is measured until they regain their righting reflexes.

Results

Among different solvent extracts (AC-1 to AC-13) subjected for pentobarbitone potentiation test, AC-1, AC-5 and AC-9, showed promising activity and the activity of AC-9 was found to be significant (FIG. 1). The extracts AC-10 to AC-13 prepared from *Hedychium spicatum* did not show any activity.

In an attempt to combine *Hedychium spicatum* extract (AC-10) to the highly active AC-9 extract to see any potentiation of the activity of AC-9, it was found surprisingly that AC-14 extract, which is a combination of AC-9 and AC-10 in a ratio of 3:1 is significantly more active than AC-9 extract. Alternatively, the combination of AC-9 and AC-10 in a ratio of 1:3 (AC-15) showed very less activity (FIG. 1). The combination extract (3:1), AC-14 is designated as SD-18 for further evaluation in preclinical and clinical evaluation.

EXAMPLE 7

Detailed Preclinical Evaluation Of SD-18 In Mice

Sleeping Time in Mice.

Groups of 8 male mice with an average weight of 25-28 g are used. They are dosed, i.p. with the test compound (SD-18) at a dose of 125, 250 and 500 mg/kg or the reference standard (pentobarbitone) at a dose of 40 mg/kg. The animals were placed on their backs on a warmed (37° C.) pad and the duration of loss of the righting reflex (starting at the time of injection) is measured until they regain their righting reflexes.

Potentiation Of Pentobarbitone Sleeping Time

Groups of 8 male mice with an average weight of 25-28 g are used. They are dosed orally, i.p. with the test compound at a dose of 25, 50, 75 and 100 mg/kg or the reference standard (e.g. 2.5 mg/kg diazepam p.o.) or the vehicle. Thirty minutes after i.p. injection, 40 mg/kg pentobarbital is injected intraperitonially. The animals are placed on their backs on a warmed (37° C.) pad and the duration of loss of the righting reflex (starting at the time of pentobarbital injection) is measured until they regain their righting reflexes.

Pentylenetetrazole (Metrazol) Induced Convulsions

Rats of either sex with a body weight between 200-225 g are used. The test compound at a dose of 500 and 750 mg/kg is administered p.o. to groups of 8 rats. Another group of 8 rats serves as control. Sixty minutes after oral administration 60 mg/kg MTZ (Metrazol) was injected subcutaneously. Each animal is placed into an individual plastic cage for observation lasting 1 h. Seizures and tonic-clonic convulsions are recorded.

Elevated Plus Maze Test

The plus-maze consists of two open arms, 50×10×40 cm, and two enclosed arms, 50×10×40 cm, with an open roof, arranged so that the two open arms are opposite to each other. The maze is elevated to a height of 50 cm. The rats (225-250 g body weight) are housed in pairs for 10 days prior to testing in the apparatus. During this time the rats are handled by the investigator on alternate days to reduce stress. Groups consist of 6 rats for each dose. Thirty minutes after i.p. administration of the test drug or the standard, the rat is placed in the center of the maze, facing one of the enclosed arms. During a 5 minutes test period the following measures are taken: the number of entries into and time spent in the open and enclosed arms; the total number of arm entries.

EXAMPLE 8

Results & Analysis

Sleeping Time in Mice

Figure 2:
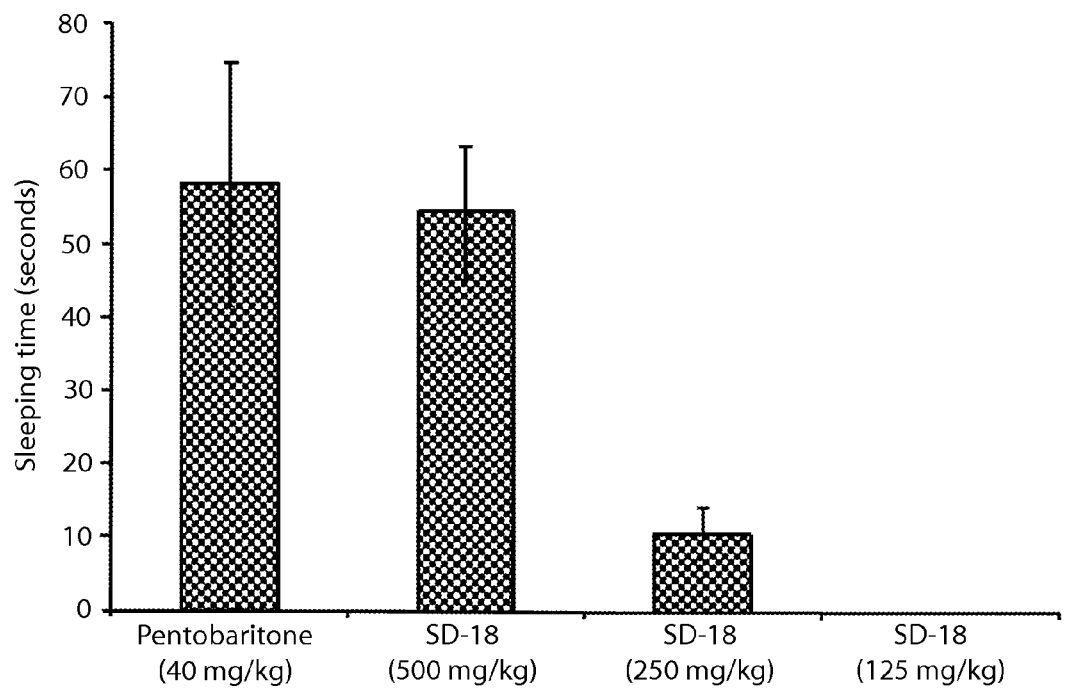
FIG. 2. Bar graph representation sowing sedative activity of SD-18 in mice.

SD-18 in mice exhibited sedative activity in dose dependent manner and dose of 500 mg/kg was equipotent to pentobarbitone of 40 mg/kg (FIG. 2).

Potentiation Of Pentobarbitone Sleeping Time

Figure 3:
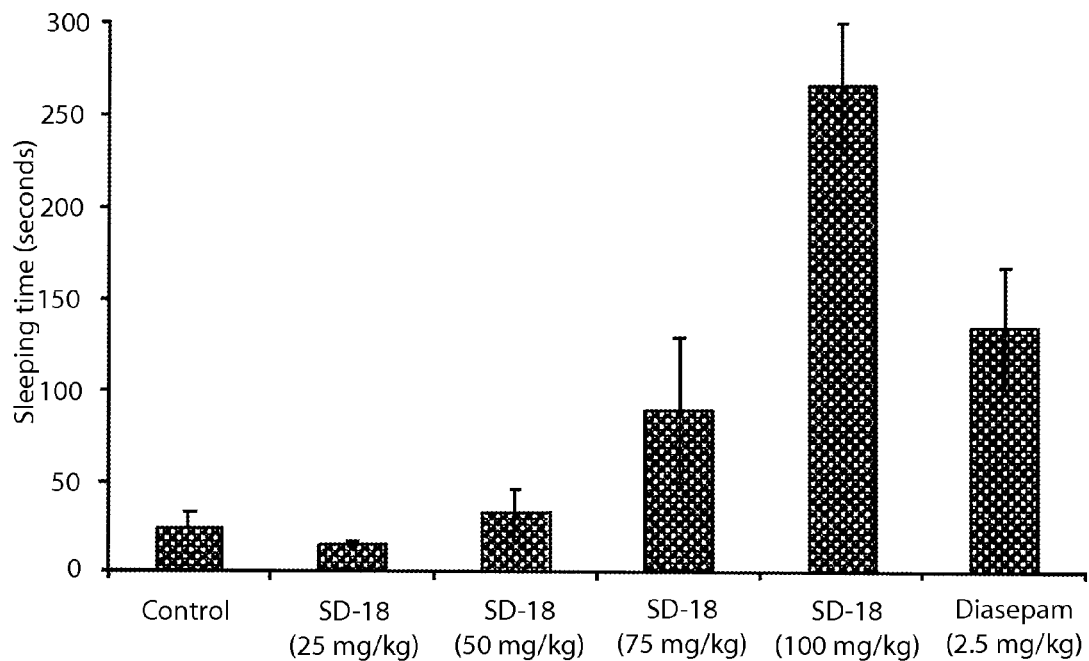
FIG. 3. Bar graph representation sowing effect of SD-18 on Pentobarbitone induced sleeping time in mice.

SD-18 potentiated pentobarbitone induced sleeping time in mice dose dependently as shown in FIG. 3.

Pentylenetetrazole (PTZ, Metrazol) Induced Convulsions

Figure 4:
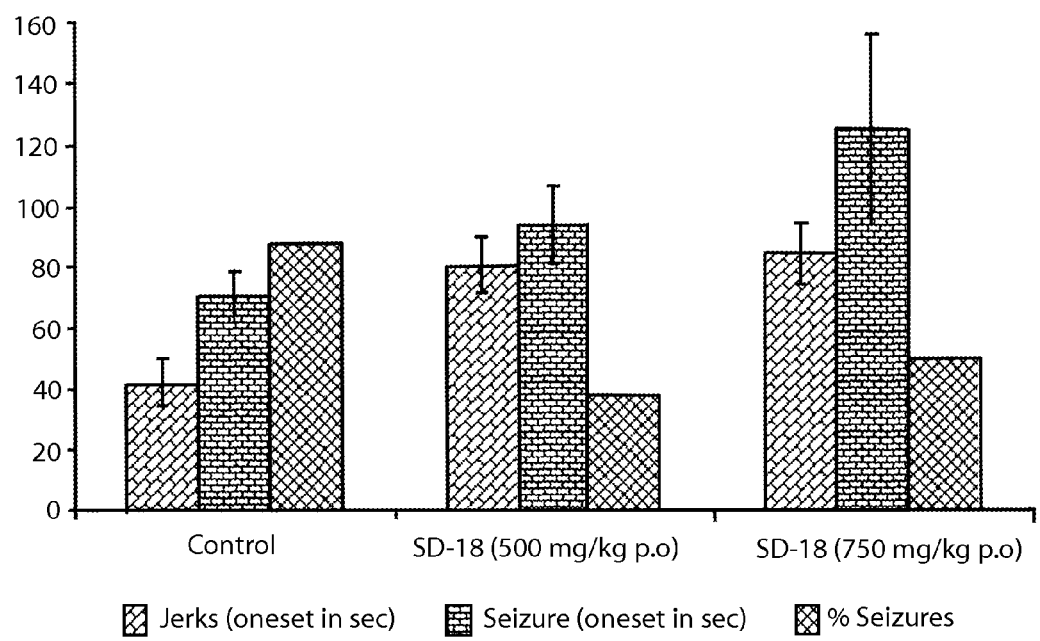
FIG. 4. Bar graph representation sowing effect of SD-18 on Pentylenetetrazole (PTZ) induced convulsion in Rats.

SD-18 significantly prolonged the onset of seizures and jerks due to PTZ in rats and also reduced percentage of animals showing seizures (FIG. 4).

Elevated Plus Maze Test

Figure 5:
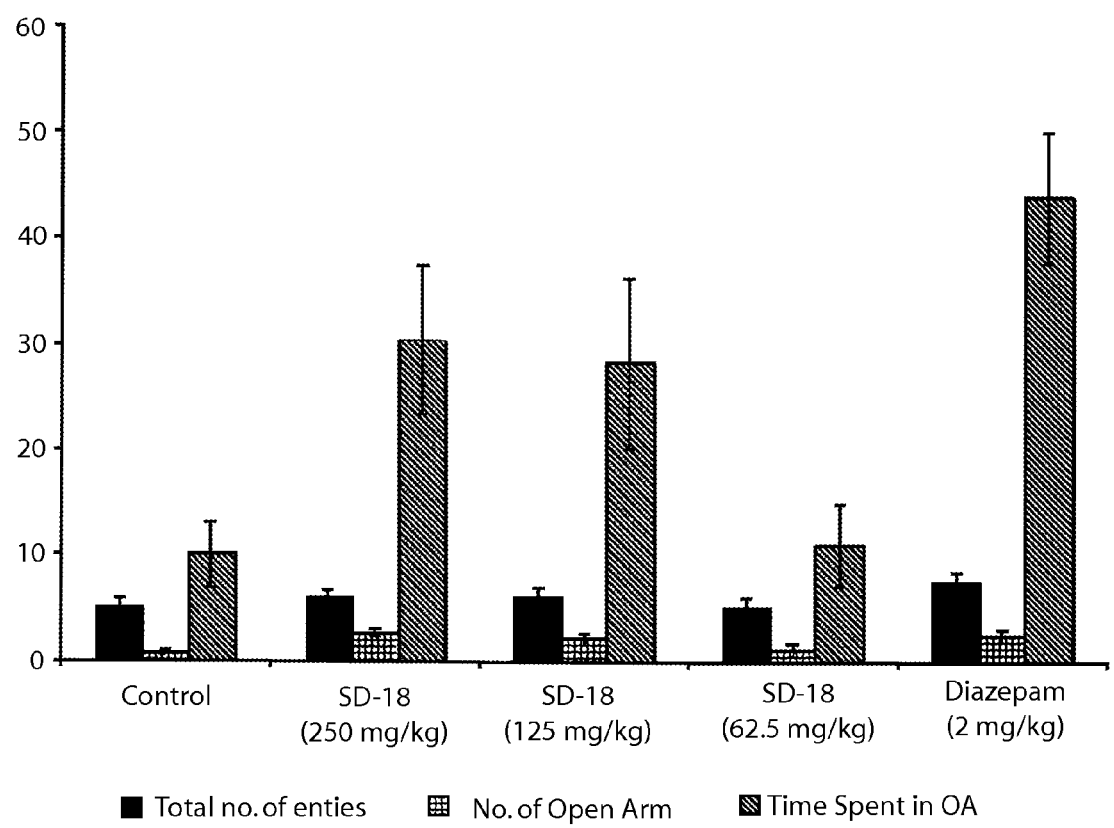
FIG. 5. Bar graph representation sowing anxiolytic effect of SD-18 on Elevated Plus maze Test.

SD-18 treatment increased the total number of arm entries, number of open arm entries and time spent in the open arms (FIG. 5).

EXAMPLE 9

Preparation of SoftGel Capsules of SD-18

Formulation

TABLE 3

| Sl. No. | Name of the ingredient | Formula I (mg) | Formula II (mg) | Formula III (mg) | Formula IV (mg) |
|---|---|---|---|---|---|
| 1. | SD-18 Extract IH | 50 | 100 | 250 | 500 |
| 2. | Ajowan Oil | 1.25 | 2.5 | 6.25 | 12.50 |

TABLE 3-continued

| Sl. No. | Name of the ingredient | Formula I (mg) | Formula II (mg) | Formula III (mg) | Formula IV (mg) |
|---|---|---|---|---|---|
| 3. | Lavender Oil | 2.5 | 5 | 12.50 | 25 |
| 4. | Butylated Hydroxy Toluene IP | 1.0 | 2.0 | 5.0 | 10.0 |
| 5. | Methyl paraben | 0.05 | 0.10 | 0.25 | 0.50 |
| 6. | Propyl paraben | 0.01 | 0.02 | 0.05 | 0.10 |

Preparation of Fill Material

SD-18 extract, Ajowan Oil and Lavender Oil were taken in the container and heated upto 40° C. on a heater to obtain a flowable liquid, then Butylated Hydroxy Toluene (BHT) was dissolved in small quantity of flowable liquid at 40 to 50° C. and added to the same in container containing flowable liquid under mixing. After mixing the liquid for 20 minutes, allowed to remain at the room temperature till oil is free of air bubbles, after that the container was closed with the proper lid tightly and attached proper status label and recorded the weight of final mixture before encapsulation.

Preparation of Gelatin Mass

Preparation of Preservative Solution

A small quantity of glycerin was taken in a SS container and heated at 60° C., Methylparaben & Propylparaben were added in SS container and stirred to dissolve, the resultant solution was strained through 100-mesh sieve, then the resultant solution, Sorbitol and Distilled water were added into the reactor, then added the Gelatin powder into reactor and switch ON the stirrer and cooked the same for 90 minutes, de-aerate the resultant gelatin mass by applying vacuum, added caramel dispersion along with titanium dioxide slurry and mixed with gelatin mass and stored the same at 55° C. until usage.

Encapsulation

Encapsulate the fill material with a Target fill weight of 50 to 500 mg by using Die size & shape 5J oval and Gel color Light Brown Opaque. In this process the gelatin mass gets extruded on 2 drums as ribbons and slides over two rotary dies. The fill material gets injected and the ribbon surface takes the shape of the die and due to pressure applied, will seal the upper end after injection. The formed capsules get detached from the net and is pneumatically conveyed to semi-drier. In the semidrier, filtered and dehumidified air is blown across the capsule and removes moisture. The capsules are unloaded on to trays.

Capsule Drying

Allow the encapsulated capsules to harden in the drying tunnel. The capsules are considered to be dry when the 8-12% moisture content in shell is achieved and can be removed from the drying tunnel at that point of time for further procession. After drying, the capsules should be immediately emptied out into airtight containers before taking up for further processing.

EXAMPLE 10

Clinical Evaluation of Efficacy and Safety of SD-18 in Refractory Insomnia in Human Beings A non-comparative clinical trial was conducted in 100 patients with refractory insomnia. Total 100 patients were included in the study and the total duration of the study was four weeks. The included patients were stratified into three groups i.e. suffering from insomnia, with refractory insomnia and post-operative insomnia. Assessment of sleep complaint was done by a detailed history of the sleep complaint, history from the bed partner, history of medications (Over-the-counter medications, recreational drug use) and psychiatric history (personal history of mood, anxiety, stress and irritability.

All patients observed sleep hygiene rules as avoiding excessively long times in bed, use of the alarm and getting up at the same time each day, seven days a week, avoiding day time naps, daily aerobic exercise of at least 30 minutes three to four hours before bedtime keeping the bedroom dark, quiet and comfortably cool, eating a little carbohydrate snack before bed, avoiding alcohol, nicotine and caffeine in the evening, avoiding drinking too much fluid in the evening to reduce the need to get up to go the bathroom. All patients were asked to take the drug (SD-18) one capsule, before bedtime daily. All patients maintained a sleep diary maintaining details regarding time into bed, time of "lights out", time to fall asleep, number of awakenings, time of "lights on", time out of bed, and total sleep time. All the patients evaluated above sleep quality parameters on a scale from zero to ten [0=Worst; 10=Best).

The analysis of the time difference between getting into bed and falling asleep by One-way analysis of variance showed that, the difference in the means for 7 groups (Days 0, 5, 10, 15, 20, 25 and 31) was significantly significant ($P<0.05$). The Bartlett's test showed that, the difference in the variances was significantly significant ($P<0.05$). The results of Dunnett's Multiple Comparison Test are shown in Table 4.

TABLE 4

| | Mean Diff. | q | P value | 95% CI of diff |
|---|---|---|---|---|
| Day 0 vs Day 5 | 0.1875 | 1.522 | P > 0.05 | −0.1292 to 0.5042 |
| Day 0 vs Day 10 | 0.2245 | 1.822 | P > 0.05 | −0.09220 to 0.5412 |
| Day 0 vs Day 15 | 0.4540 | 3.684 | P < 0.001 | 0.1373 to 0.7707 |
| Day 0 vs Day 20 | 0.5130 | 4.163 | P < 0.001 | 0.1963 to 0.8297 |
| Day 0 vs Day 25 | 0.5430 | 4.406 | P < 0.001 | 0.2263 to 0.8597 |
| Day 0 vs Day 31 | 0.5270 | 4.277 | P < 0.001 | 0.2103 to 0.8437 |

The analysis of the time difference between putting lights off and falling asleep by One-way analysis of variance showed that, the difference in the means for 7 groups (Days 0, 5, 10, 15, 20, 25 and 31) was significantly significant ($P<0.05$). The Bartlett's test showed that, the difference in the variances was significantly significant ($P<0.05$). The results of Dunnett's Multiple Comparison Test are shown in Table 5.

TABLE 5

| | Mean Diff. | q | P value | 95% CI of diff |
|---|---|---|---|---|
| Day 0 vs Day 5 | 0.1165 | 2.293 | P > 0.05 | −0.01410 to 0.2471 |
| Day 0 vs Day 10 | 0.1635 | 3.217 | P < 0.001 | 0.03290 to 0.2941 |
| Day 0 vs Day 15 | 0.2675 | 5.264 | P < 0.001 | 0.1369 to 0.3981 |
| Day 0 vs Day 20 | 0.2920 | 5.746 | P < 0.001 | 0.1614 to 0.4226 |
| Day 0 vs Day 25 | 0.2990 | 5.884 | P < 0.001 | 0.1684 to 0.4296 |
| Day 0 vs Day 30 | 0.3035 | 5.972 | P < 0.001 | 0.1729 to 0.4341 |

The analysis of the number of awakenings by One-way analysis of variance showed that, the difference in the means for 7 groups (Days 0, 5, 10, 15, 20, 25 and 31) was significantly significant ($P<0.05$). The Bartlett's test showed that, the difference in the variances was significantly significant ($P<0.05$). The results of Dunnett's Multiple Comparison Test are shown in Table 6.

TABLE 6

|  | Mean Diff. | q | P value | 95% CI of diff |
|---|---|---|---|---|
| Day 0 vs Day 5 | 0.3400 | 3.076 | P < 0.05 | 0.05590 to 0.6241 |
| Day 0 vs Day 10 | 0.9000 | 8.141 | P < 0.001 | 0.6159 to 1.184 |
| Day 0 vs Day 15 | 1.200 | 10.86 | P < 0.001 | 0.9159 to 1.484 |
| Day 0 vs Day 20 | 1.660 | 15.02 | P < 0.001 | 1.376 to 1.944 |
| Day 0 vs Day 25 | 1.890 | 17.10 | P < 0.001 | 1.606 to 2.174 |
| Day 0 vs Day 31 | 1.827 | 16.53 | P < 0.001 | 1.543 to 2.111 |

The analysis of the rating for overall feeling by One-way analysis of variance showed that, the difference in the means for 7 groups (Days 0, 5, 10, 15, 20, 25 and 31) was significantly significant (P<0.05). The Bartlett's test showed that, the difference in the variances was significantly significant (P<0.05). The results of Dunnett's Multiple Comparison Test are shown in Table 7.

TABLE 7

|  | Mean Diff. | q | P value | 95% CI of diff |
|---|---|---|---|---|
| Day 0 vs Day 5 | −0.3100 | 2.927 | P < 0.05 | −0.5822 to −0.03779 |
| Day 0 vs Day 10 | −0.6400 | 6.042 | P < 0.001 | −0.9122 to −0.3678 |
| Day 0 vs Day 15 | −1.010 | 9.535 | P < 0.001 | −1.282 to −0.7378 |
| Day 0 vs Day 20 | −1.480 | 13.97 | P < 0.001 | −1.752 to −1.208 |
| Day 0 vs Day 25 | −1.920 | 18.13 | P < 0.001 | −2.192 to −1.648 |
| Day 0 vs Day 31 | −2.120 | 20.02 | P < 0.001 | −2.392 to −1.848 |

The analysis of irritable feeling by One-way analysis of variance showed that, the difference in the means for 7 groups (Days 0, 5, 10, 15, 20, 25 and 31) was significantly significant (P<0.05). The Bartlett's test showed that, the difference in the variances was significantly significant (P<0.05). The results of Dunnett's Multiple Comparison Test are shown in Table 8.

TABLE 8

|  | Mean Diff. | Q | P value | 95% CI of diff |
|---|---|---|---|---|
| Day 0 vs Day 5 | 0.4100 | 3.776 | P < 0.00 | 0.1310 to 0.6890 |
| Day 0 vs Day 10 | 0.9200 | 8.473 | P < 0.001 | 0.6410 to 1.199 |
| Day 0 vs Day 15 | 1.300 | 11.97 | P < 0.001 | 1.021 to 1.579 |
| Day 0 vs Day 20 | 1.790 | 16.49 | P < 0.001 | 1.511 to 2.069 |
| Day 0 vs Day 25 | 2.260 | 20.81 | P < 0.001 | 1.981 to 2.539 |
| Day 0 vs Day 31 | 2.530 | 23.30 | P < 0.001 | 2.251 to 2.809 |

The analysis of the total sleep duration by One-way analysis of variance showed that, the difference in the means for 7 groups (Days 0, 5, 10, 15, 20, 25 and 31) was significantly significant (P<0.05). The Bartlett's test showed that, the difference in the variances was significantly significant (P<0.05). The results of Dunnett's Multiple Comparison Test are shown in Table 9.

TABLE 9

|  | Mean Diff. | Q | P value | 95% CI of diff |
|---|---|---|---|---|
| Day 0 vs Day 5 | −0.2765 | 1.451 | P > 0.05 | −0.7664 to 0.2134 |
| Day 0 vs Day 10 | −0.7985 | 4.189 | P < 0.001 | −1.288 to −0.3086 |
| Day 0 vs Day 15 | −1.493 | 7.830 | P < 0.001 | −1.982 to −1.003 |
| Day 0 vs Day 20 | −1.644 | 8.622 | P < 0.001 | −2.133 to −1.154 |
| Day 0 vs Day 25 | −2.041 | 10.71 | P < 0.001 | −2.531 to −1.551 |
| Day 0 vs Day 31 | −2.264 | 11.87 | P < 0.001 | −2.753 to −1.774 |

The analysis of the sleep quality by One-way analysis of variance showed that, the difference in the means for 7 groups (Days 0, 5, 10, 15, 20, 25 and 31) was significantly significant (P<0.05). The Bartlett's test showed that, the difference in the variances was significantly significant (P<0.05). The results of Dunnett's Multiple Comparison Test are shown in Table 10.

TABLE 10

|  | Mean Diff. | Q | P value | 95% CI of diff |
|---|---|---|---|---|
| Day 0 vs Day 5 | −1.700 | 10.25 | P < 0.001 | −2.126 to −1.274 |
| Day 0 vs Day 10 | −3.740 | 22.56 | P < 0.001 | −4.166 to −3.314 |
| Day 0 vs Day 15 | −5.420 | 32.69 | P < 0.001 | −5.846 to −4.994 |
| Day 0 vs Day 20 | −6.600 | 39.81 | P < 0.001 | −7.026 to −6.174 |
| Day 0 vs Day 25 | −7.310 | 44.09 | P < 0.001 | −7.736 to −6.884 |
| Day 0 vs Day 31 | −7.558 | 32.12 | P < 0.001 | −8.163 to −6.953 |

Statistical Analysis

TABLE 11

| Time bed-time asleep | | | | | | | |
|---|---|---|---|---|---|---|---|
|  | Day 0 | Day 5 | Day 10 | Day 15 | Day 20 | Day 25 | Day 31 |
| MEAN | 1.198 | 1.0105 | 0.9735 | 0.744 | 0.685 | 0.655 | 0.671 |
| STDEV | 0.637741 | 0.578674 | 1.943124 | 0.464349 | 0.454245 | 0.449382 | 0.416768 |
| SEM | 0.063774 | 0.057867 | 0.194312 | 0.046435 | 0.045424 | 0.044938 | 0.041677 |
| p Value | P < 0.0001 | | | | | | |
| Significance | *** | | | | | | |

TABLE 12

| No. of awakenings | | | | | | | |
|---|---|---|---|---|---|---|---|
|  | Day 0 | Day 5 | Day 10 | Day 15 | Day 20 | Day 25 | Day 31 |
| MEAN | 1.97 | 1.63 | 1.07 | 0.77 | 0.31 | 0.08 | 0.143 |
| STDEV | 0.642831 | 1.160416 | 0.807227 | 0.789515 | 0.734366 | 0.307482 | 0.780087 |
| SEM | 0.064283 | 0.116042 | 0.080723 | 0.078951 | 0.073437 | 0.030748 | 0.078009 |
| P Value | P < 0.0001 | | | | | | |
| Significance | *** | | | | | | |

TABLE 13

Irritability

|  | Day 0 | Day 5 | Day 10 | Day 15 | Day 20 | Day 25 | Day 31 |
| --- | --- | --- | --- | --- | --- | --- | --- |
| MEAN | 4.1 | 3.69 | 3.18 | 2.8 | 2.31 | 1.84 | 1.57 |
| STDEV | 0.797724 | 0.761378 | 0.6724 | 0.752101 | 0.747994 | 0.646982 | 0.95616 |
| SEM | 0.079772 | 0.076138 | 0.06724 | 0.07521 | 0.074799 | 0.064698 | 0.095616 |
| P Value | $P < 0.0001$ | | | | | | |
| Significance | *** | | | | | | |

TABLE 14

Sleep Quality

|  | Day 0 | Day 5 | Day 10 | Day 15 | Day 20 | Day 25 | Day 31 |
| --- | --- | --- | --- | --- | --- | --- | --- |
| MEAN | 1.26 | 2.96 | 5 | 6.68 | 7.86 | 8.57 | |
| STDEV | 1.031034 | 1.062872 | 1.287076 | 1.462529 | 1.197809 | 0.987344 | |
| SEM | 0.103103 | 0.106287 | 0.128708 | 0.146253 | 0.119781 | 0.098734 | |
| P Value | $P < 0.0001$ | | | | | | |
| Significance | *** | | | | | | |

TABLE 15

Time lightoff - asleep

|  | Day 0 | Day 5 | Day 10 | Day 15 | Day 20 | Day 25 | Day 30 |
| --- | --- | --- | --- | --- | --- | --- | --- |
| MEAN | 0.555 | 0.4385 | 0.3915 | 0.2875 | 0.263 | 0.256 | 0.2515 |
| STDEV | 0.507544 | 0.406876 | 0.501365 | 0.232941 | 0.256296 | 0.246212 | 0.220817 |
| SEM | 0.050754 | 0.040688 | 0.050136 | 0.023294 | 0.02563 | 0.024621 | 0.022082 |
| p Value | $P < 0.0001$ | | | | | | |
| Significance | *** | | | | | | |

TABLE 16

Rate how you felt today?*

|  | Day 0 | Day 5 | Day 10 | Day 15 | Day 20 | Day 25 | Day 31 |
| --- | --- | --- | --- | --- | --- | --- | --- |
| MEAN | 1.34 | 1.65 | 1.98 | 2.35 | 2.82 | 3.26 | 3.46 |
| STDEV | 0.476095 | 1.192358 | 0.550115 | 0.625631 | 0.657206 | 0.74698 | 0.770937 |
| SEM | 0.04761 | 0.119236 | 0.055011 | 0.062563 | 0.065721 | 0.074698 | 0.077094 |
| p Value | $P < 0.0001$ | | | | | | |
| Significance | *** | | | | | | |

TABLE 17

Total Sleep Duration

|  | Day 0 | Day 5 | Day 10 | Day 15 | Day 20 | Day 25 | Day 31 |
| --- | --- | --- | --- | --- | --- | --- | --- |
| MEAN | 5.3765 | 5.653 | 6.175 | 6.869 | 7.02 | 7.4175 | 7.64 |
| STDEV | 0.856687 | 0.82081 | 0.636138 | 3.106598 | 0.616155 | 0.6591 | 0.663173 |
| SEM | 0.085669 | 0.082081 | 0.063614 | 0.31066 | 0.061615 | 0.06591 | 0.066317 |
| p Value | $P < 0.0001$ | | | | | | |
| Significance | *** | | | | | | |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A sedative composition for treating anxiety, stress, convulsions, sleep disorders and interrupted sleep comprising a *Myristica fragrans* plant extract and a *Hedychium spicatum* plant extract, wherein the *Myristica fragrans* plant extract is a petroleum ether, methanol or ethanol extract of *Myristica fragrans* seeds and wherein the *Hedychium spicatum* plant extract is an n-hexane, chloroform, ethyl alcohol or methanol extract of *Hedychium spicatum* rhizome.

2. The sedative composition according to claim 1, the composition further comprising ajowan oil, lavender oil, butylated hydroxy toluene, methyl paraben sodium and propyl paraben sodium.

3. The sedative composition according to claim 1, wherein the ratio of the *Myristica fragrans* plant extract and the *Hedychium spicatum* plant extract is about 3:1.

4. The sedative composition according to claim 1, the composition comprising about 3 parts of the *Myristica fragrans* plant extract, about 1 part of the *Hedychium spicatum* plant extract, the composition further comprising about 2.5 weight % ajowan oil, about 5 weight % lavender oil and other pharmaceutically acceptable carriers.

5. The sedative composition according to claim 1, the composition comprising the *Myristica fragrans* plant extract, the *Hedychium spicatum* plant extract, ajowan oil and lavender oil in an amount of 50 mg to 500 mg, the composition further comprising about 0.02 weight % of butylated hydroxy toluene, about 0.01 mg of methyl paraben sodium and about 0.0025 mg propyl paraben sodium.

6. The sedative composition according to claim 1, wherein the composition is an oral dosage form.

7. The sedative composition according to claim 6, wherein the oral dosage form is selected from the group consisting of tablets, softgel capsules, granules, powders, concentrates, syrups, and combinations thereof.

8. The sedative composition according to claim 7, wherein the oral dosage form is softgel capsules.

9. A method for treating anxiety, stress, convulsions, sleep disorders and interrupted sleep by administering a patient a therapeutically effective amount of the sedative composition of claim 1.

10. The method of claim 9, wherein the sedative composition further comprises ajowan oil, lavender oil and a pharmaceutically acceptable carrier.

11. A process for obtaining a sedative composition, the process comprising extracting a *Myristica fragrans* seed with petroleum ether, methanol or ethanol to obtain a *Myristica fragrans* plant extract, extracting *Hedychium spicatum* rhizome with n-hexane, chloroform, ethyl alcohol or methanol to obtain a *Hedychium spicatum* plant extract, and combining said *Myristica fragrans* plant extract and said *Hedychium spicatum* plant extract to form a sedative composition.

12. The process for obtaining a sedative composition according to claim 11, wherein said extracting a *Myristica fragrans* seed is performed by percolation or hot soxhalation, and wherein the process further comprises concentrating the *Myristica fragrans* plant extract.

13. The process for obtaining a sedative composition according to claim 11, wherein said extracting a *Hedychium spicatum* rhizome is performed by percolation or hot soxhalation, and wherein the process further comprises concentrating the *Hedychium spicatum* plant extract.

14. The process for obtaining a sedative composition of claim 11, the process further comprising adding ajowan oil, lavender oil and a pharmaceutically acceptable carrier to the sedative composition.

* * * * *